United States Patent [19]
Williams

[11] Patent Number: 5,232,024
[45] Date of Patent: Aug. 3, 1993

[54] SLIDE-VALVE MANIFOLD

[76] Inventor: Eli Williams, 677 W. 3400 South, Bountiful, Utah 84010

[21] Appl. No.: 707,670

[22] Filed: May 30, 1991

[51] Int. Cl.⁵ .............................................. F16K 11/00
[52] U.S. Cl. .................................. 137/883; 137/606; 604/82
[58] Field of Search .................. 137/606, 883; 604/30, 604/33, 249, 82

[56] References Cited

U.S. PATENT DOCUMENTS

3,859,985  1/1975  Eckhart ........................... 604/33 X
4,423,741  1/1984  Levy ................................ 604/249 X Primary Examiner—John C. Fox
Attorney, Agent, or Firm—Trask, Britt & Rossa

[57] ABSTRACT

A slide-valve manifold useful for attachment to a catheter and a syringe is disclosed. The slide-valve construction of the manifold tolerates high-pressure fluid without significant leakage. The manifold may contain a single slide element or multiple slide elements.

5 Claims, 7 Drawing Sheets

SLIDE-VALVE MANIFOLD

BACKGROUND OF THE INVENTION

Field

The invention relates to manifold valves utilized in medical procedures for injection and withdrawal of selected fluids to and from a patient. Such manifold valves are constructed to interact with a syringe on one end and a catheter on the other end.

State of the Art

Manifold-type valves which interact with a syringe, which have multiple ports for communicating with various liquid containers, to inject and withdraw selected fluids into and from a patient, are known in the art.

Figure 9:
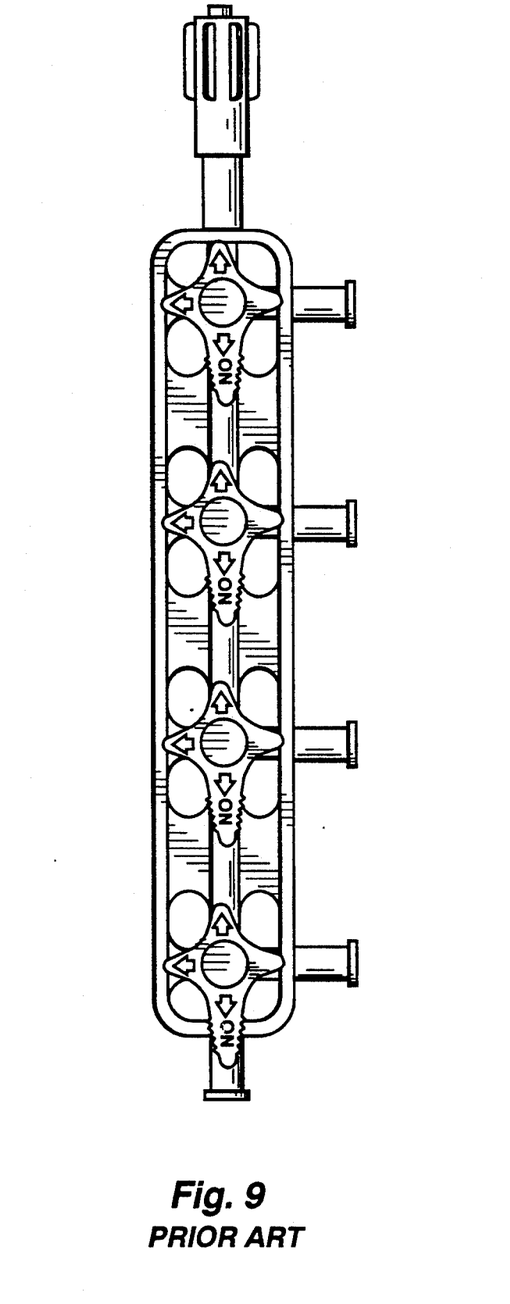
FIG. 9 is a perspective view of a typical prior art manifold valve body having individual petcocks.

A typical manifold-type valve consists of a valve body having a central main bore along a longitudinal axis of the manifold body and side ports which selectively communicate with the main bore by means of petcock-type valves. A manifold valve body of this type is illustrated in FIG. 9. The individual petcocks rotate from one position to another. All bores are in the same plane.

This type of manifold valve has been effective generally; however, recent procedures employing fluid pressures greater than 500 psi cause fluid leakage around the petcocks.

The petcock-type manifold is frequently used in conjunction with a balloon catheter-syringe assembly. Also, it is used in conjunction with dye injections whereby the dye or other fluid is observed on a cathode ray tube (CRT) display screen. When conducting such medical procedures, the light in the operating room is typically very dim so that the screens are readily visible. Consequently, it is difficult to see the position of the valve indicator on the petcock-type device of FIG. 9. It is difficult to determine by touch or feel of the petcock valves the exact position of the valve. Thus, not only do manifolds employing petcock valves have restrictive pressure limitations, the use of such manifolds in dim light presents operational difficulties.

Figure 10:
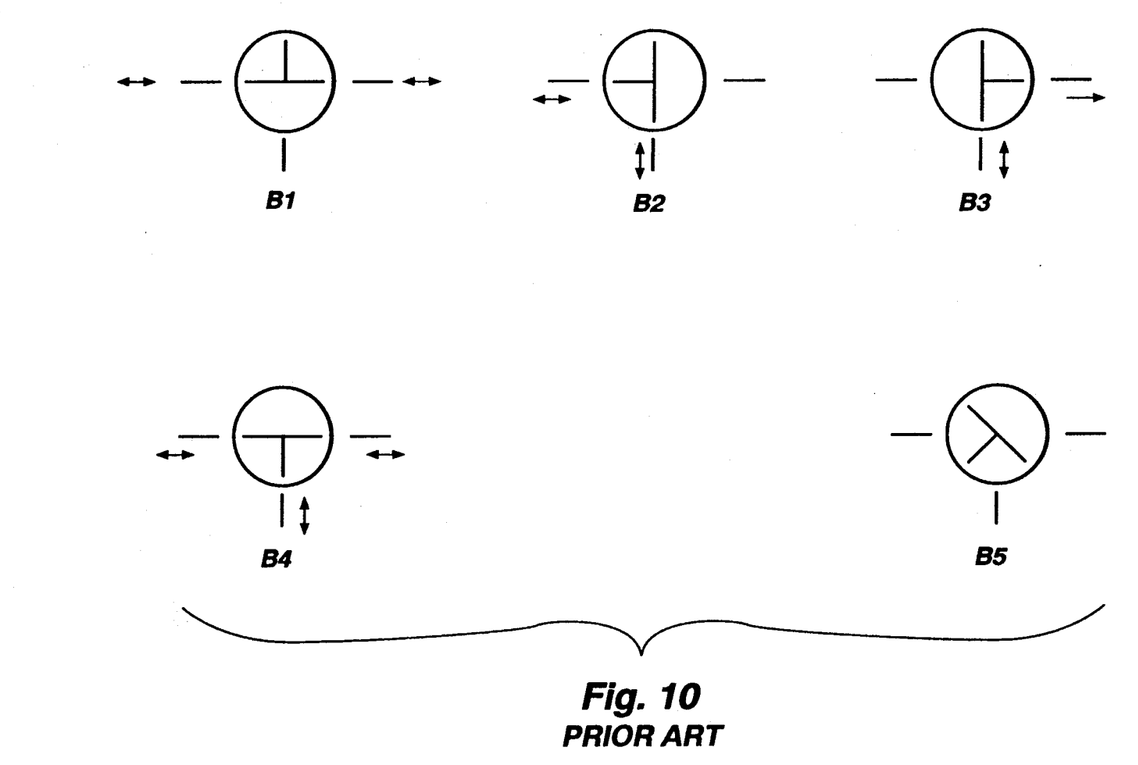
FIG. 10 illustrates various petcock valve positions, B1, B2, B3, B4 and B5, in reference to a main axial bore and a side-port bore.

The difficulties in determining the precise position of a petcock-type valve is illustrated in FIGS. 10, B1, B2, B3, B4 and B5. Thus, even with an indicator on the petcock valve handle, the precise position of the "T"-shaped bore may be difficult to determine. As can readily be observed, valve positions B1, B2 and B3 all represent valve positions wherein fluid pressure within the valve bores may result in leakage from the bore which does not communicate with another bore.

SUMMARY OF THE INVENTION

The instant invention involves a manifold-type valve which can be connected to a syringe for the purpose of withdrawing and injecting various fluids into and from a patient. Typically, the manifold has one injection port which is the main outlet port for the manifold, a syringe connection port (inlet port) and a plurality of side or ancillary ports which connect to various selected fluids for injection into a patient during a prescribed medical procedure or which connect to waste containers to hold fluids withdrawn from a patient.

Manifold-type valves generally permit various fluids to be injected and withdrawn, in seriatim, without detaching any of the tubes, cannulas, syringes, manifolds, etc. from the patient. The instant invention is especially useful inasmuch as a slide-valve manifold permits rapid switching from one fluid injection or withdrawal to another and permits a very high pressure to be applied to the fluids, for example, pressures up to 1,000 psi without fluid leakage from the manifold.

The manifold-type valve of the instant invention generally has means to interact with a syringe and various liquid media sources or waste container, and comprises a manifold body which is generally an elongated body with a main bore extending along a central longitudinal axis. The main bore has an external opening at one end of the manifold body which is or interconnects with a syringe port and which may have means associated with that external opening which connects to a syringe, e.g., a bayonet or luer connector. The manifold body also has one or more slide members which operate within said valve body to interact with the main axial bore to interconnect that bore with a discharge (injection) port, or with one of the ancillary ports for withdrawing or discharging a selected fluid. Slide members may, alternatively, be placed in communication with transverse bores which are lateral offshoots of the main bore.

Further description of the invention may be facilitated by reference to the attached drawings.

DETAILED DESCRIPTION OF THE INVENTION

Figure 1:
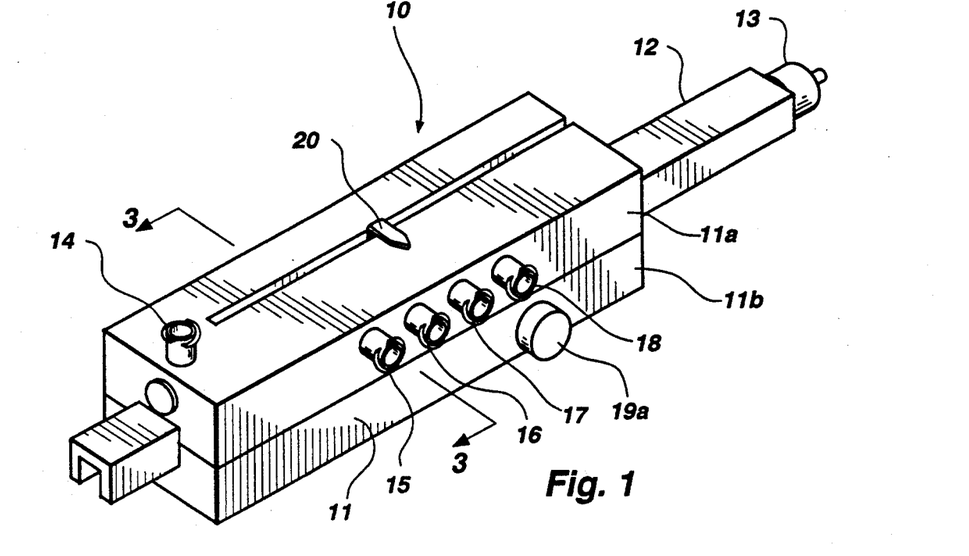
FIG. 1 is a perspective view of a slide-valve manifold embodying the instant invention.
Figure 2:
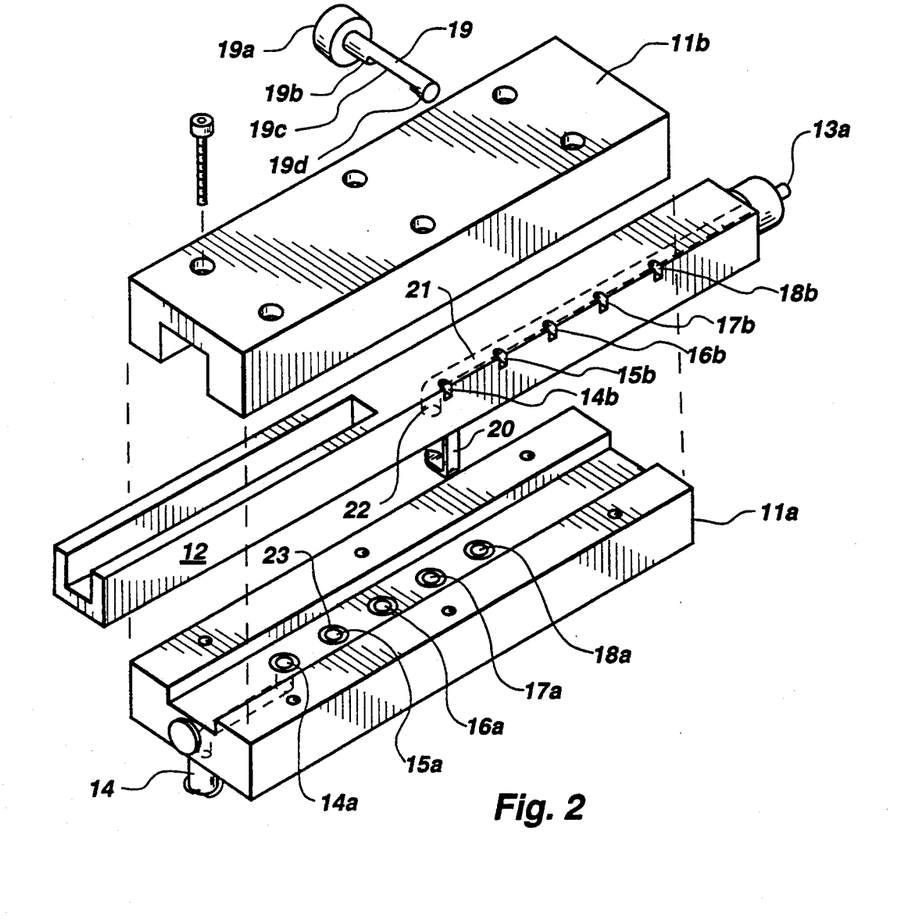
FIG. 2 is a perspective, exploded view of the slide-valve manifold of FIG. 1 with the manifold having been rotated 180°.

FIG. i is a perspective view of a slide-valve manifold 10 which has a body 11 composed of an upper segment 11A and a lower segment 11B The body 11 is formed by joining the upper and lower segments 11A and 11B together, as is more fully illustrated in FIG. 2, which is an exploded, perspective view of the slide-valve manifold. The body 10 interacts with the slide member 12 which generally has a length exceeding the length of the body 10. The slide member 12 fits within a trough or channel, more fully illustrated in FIG. 2, which is sized to form a snug fit with the slide member 12. Slide member 12 has a syringe attachment joint 13 for attachment to a syringe useful for withdrawing and injecting liquids.

The valve body is further equipped with an discharge port 1 ∧ G4. In one position of the slide elements 12, the ejection port 14 is in register with a transverse opening 22 (illustrated in FIG. 2) in the upper surface of the slide member 12 which communicates with an elongated main bore, located generally along the central longitudinal axis of the slide member 12, which opens at the syringe joint 13, e.g. a bayonet-type connector, to facilitate communication with a syringe attached to such joint 13. Thus, when a syringe is attached to the syringe joint and the slide element 12 is positioned to have its discharge opening in register with discharge port 14, fluid may be caused to flow from the syringe, through the axial bore in the slide element 12, and to discharge through discharge port 14.

The manifold body 10 is further equipped with side ports 15, 16, 17, and 18. These side ports are connected through an internal, angled ("L"-shaped) bore to communicate also with the discharge opening 22 in the slide element 12 when the slide element is retracted to certain selected positions wherein the single discharge opening (more fully illustrated in FIG. 3) is in communication with one of the ancillary ports 15, 16, 17 or 18 A locking mechanism locks the slide element 12 in various selected positions so that its transverse opening 22 is in register with one of the internal ports 14a, 15a, 16a, 17a or 18a which communicate, respectively, with external ports 14, 15, 16, 17 and 18. The locking mechanism is manually operated by a knob 19 which may be structured so that it can be rotated or withdrawn so that the slide element 12 may be permitted to slide and then locked into position so that the transverse opening 22 of the slide element is in register with one of the aforesaid ports. An index marker 20 is illustrated which is attached internally to the slide element 12 to indicate which of the ancillary or side ports 15, 16, 17 or 18 is communicating with the discharge opening in the slide element 12.

The discharge port 14 could be located alongside port 15, for example, although it is generally preferred to have the port 14 remote from the other ports. Generally, port 14 is connected, through tubing and the like, to a patient who is to receive fluid passing through the slide valve manifold, or from which body fluid is to be withdrawn.

FIG. 2 is an exploded view of the slide valve manifold of the type illustrated in FIG. 1 wherein the illustration of FIG. 1 is rotated 180° so that the lower element 11B is illustrated as being above the upper element 11A. The slide element 12 has a central axial bore 21 which is shown in dotted lines, which runs along the central longitudinal axis of the slide element 12. It has an opening nozzle 13A which is adapted to interact with the syringe to receive fluids from said syringe.

The axial bore extends a sufficient distance along the slide element to permit the slide element to cause the transverse port 22 of the bore to cooperate with any of the interior openings 14A, 15A, 16A, 17A, 18A, which communicate respectively with ports 14, 15, 16, 17, and 18. An "O"-ring 23 is positioned around each interior opening 14A, 15A, 16A, 17A, and 18A to effect a pressure-tight seal between the said interior opening and discharge port 22. Although not illustrated, port 22 preferably also has a rubber "O"-ring encircling its opening.

Locking mechanism 19 has a knob 19A and a rod-like stem 19B which has a land 19C, that is, a flat area intermediate the ends of 19B, said land 19C being at least about the same width as the width of the slide element 12. The end of the locking member forms a peg-like portion 19D formed between the end of the rod 19B and the land portion 19C. The peg-like end 19D fits within notches 14B, 15B, 16B, 17B and 18B to align slide transverse port 22 with one of the ports 14A, 15A, 16A, 17A or 18A. Generally, the locking mechanism 19 is spring biased so that upon pushing inward on knob 19A, the peg 19B is disengaged from one of the notches, thereby permitting the slide member to be slid in either a forward or backward motion so that the transverse port 22 may be aligned with a selected opening 14A, 15A, 16A, 17A, or 18A.

The slide element 12 fits within a trough 12A (see FIG. 3) which is formed by molding or planing a pair of substantially identical shallow troughs 12B and 12C (see FIG. 2) on each interior surface of body valves 11A and 11B.

Figure 3:
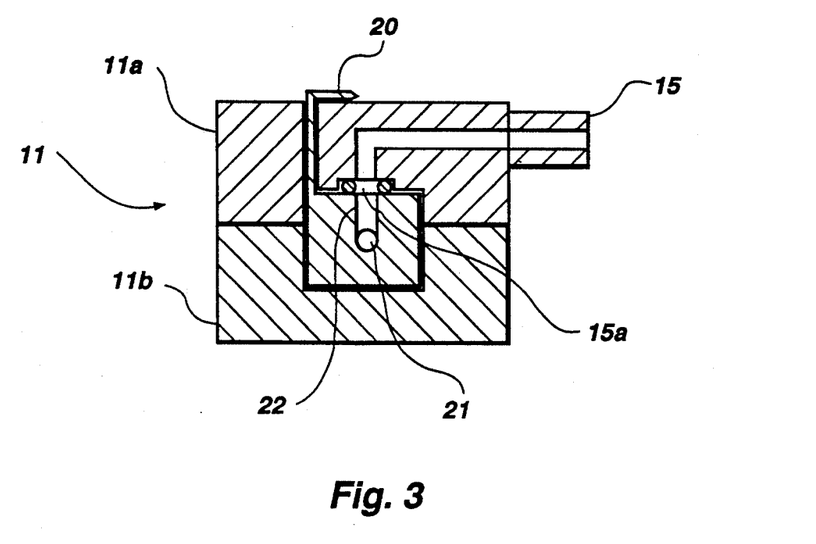
FIG. 3 is a cross-sectional view of the slide-valve manifold of FIG. 1 along section lines 3—3.

FIG. 3 is a cross-sectional view of the sliding valve manifold illustrated by FIG. 1 along section lines 3—3. The upper element 11A and the lower element 11B are shown clamped together to form the manifold body 11. The slide member is in a position wherein transverse port opening 22 is aligned with opening 15A so that fluid may either be drawn through port 15 or discharged through said port from the axial bore 21. The index marker 20 in this instance is aligned with port (nozzle) 15.

Figure 4:
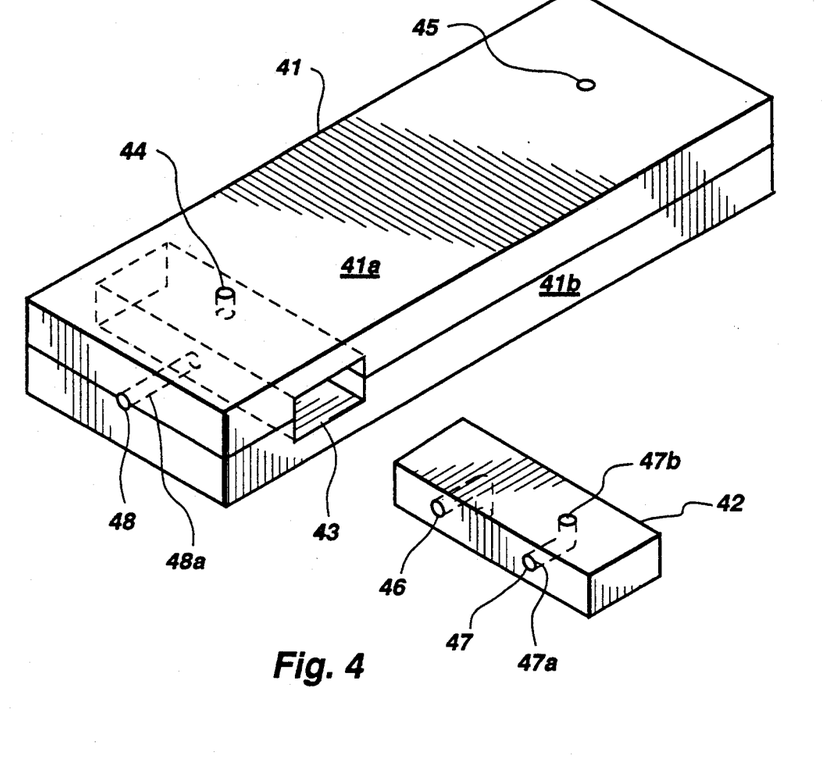
FIG. 4 is a perspective view of a slide-valve manifold employing a plurality of individual slide-valve elements.

An alternative embodiment to the central slide valve manifold is illustrated in FIG. 4. The manifold body 41 is composed of an upper element 41A and a lower element 41B. A plurality of slide members 42 fit within spaced cavities 43 which are transverse to the main longitudinal axis of the manifold body 41. Each cavity 43 is sized and adapted to receive a slide member 42 in a precise snug fit. An axial bore 48a extends a selected distance along the longitudinal axis of the manifold body 41. A transverse (vertical) bore 44 communicates between the upper surface of upper element 41A and the cavity 43. The bore 44 may communicate with a port or nozzle located on the upper surface of 41A which connects to an ancillary supply of a liquid medium. A discharge port 45 is illustrated at an opposite end from opening 48. Opening 48 may be fitted with a nozzle which is adapted to interact with a syringe member. Discharge port 45 may be fitted with a nozzle so that it may communicate with a patient.

The slide member 42 has a transverse bore 46 which, in a preselected position, communicates with axial bore 48a so that a fluid passing through axial bore 48a may pass directly through bore 46 and continue traveling through axial bore 48a. In the event the flow in bore 48a is diverted to port 44, the slide element 42 is positioned so that right angle bore 47 has its one opening 47A aligned with axial bore 48a and its upper opening 47B aligned with bore 44. A locking or indexing means similar to that illustrated in FIGS. 1-3 may be utilized with the slide member 42 so that the alignment of the bores within the slide element 42 may be precisely aligned or in register with selected bores 48 or 44.

Figure 5:
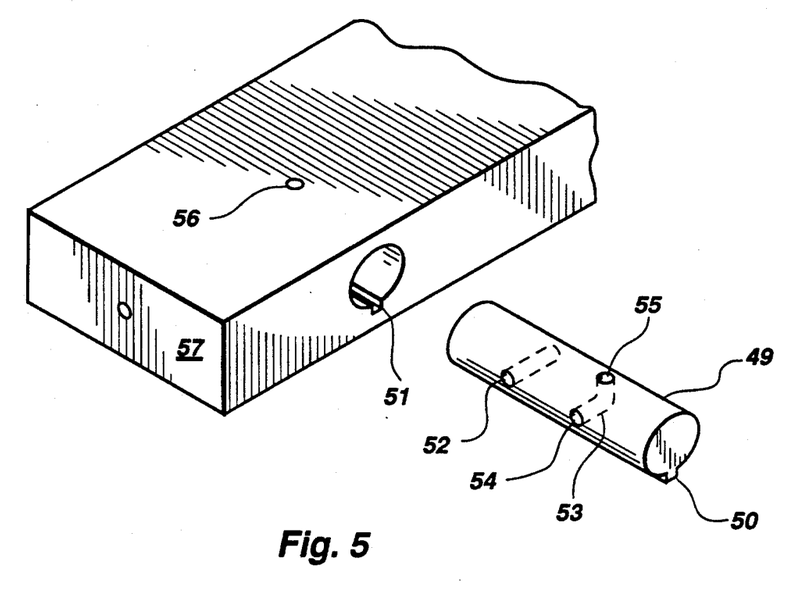
FIG. 5 is a perspective view of an alternative embodiment of the slide-valve elements of FIG. 4.

In FIG. 5, an alternative embodiment to that illustrated in FIG. 4 is shown wherein slide valve member 4 is a rod-like (round) element with a key 50 and keyway 51 to keep the slide valve oriented with reference to the manifold body. Bore 52 is transverse to the longitudinal axis of member 49 and is positioned and adapted to communicate with main bore 48a when in a closed position, i.e., it acts as an extension of bore 48a. Bore 53 is a 90° angle bore which has opening 54 adapted and positioned to communicate with main bore 48a and opening 55 adapted and positioned to communicate with ancillary discharge/inlet post 56 located in the top of manifold body 57.

An advantageous feature of the manifold device of FIGS. 4 and 5 is that high pressure fluid is never "deadheaded" within the manifold valves. Whenever bore 46 is in a position to have fluid flowing through it, then bore 47 contains no high pressure fluid and vice-versa. This is in contrast to the prior art petcock design wherein the internal bore of the petcock is "T"-shaped so that high pressure fluid is often "deadheaded," i.e., a bore contains fluid under high pressure but the bore is not in communication with another bore but is against the valve walls.

Figure 6:
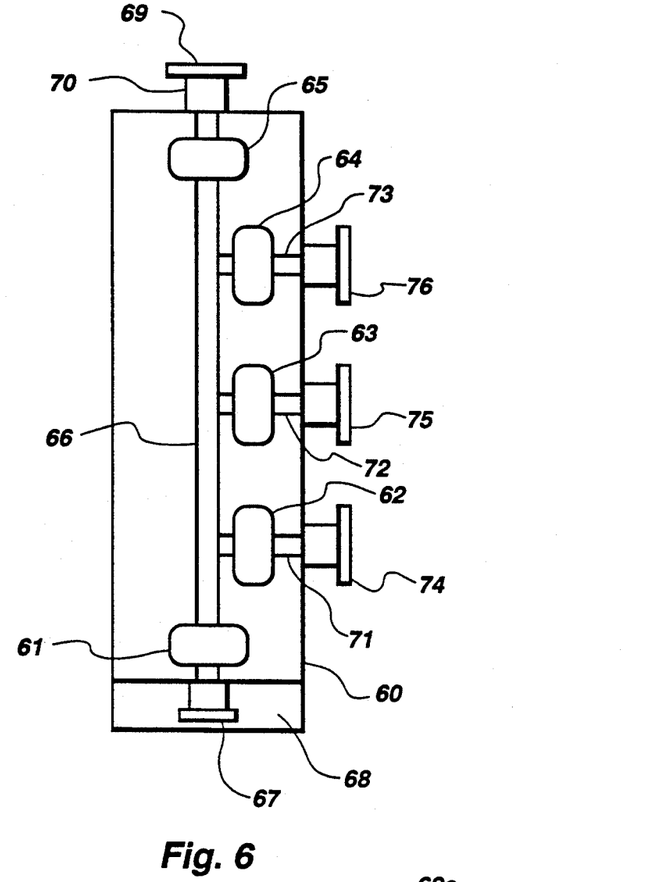
FIG. 6 is a plan view of a manifold having slide valve elements in communication with transverse bores and the main bore.
Figure 7:
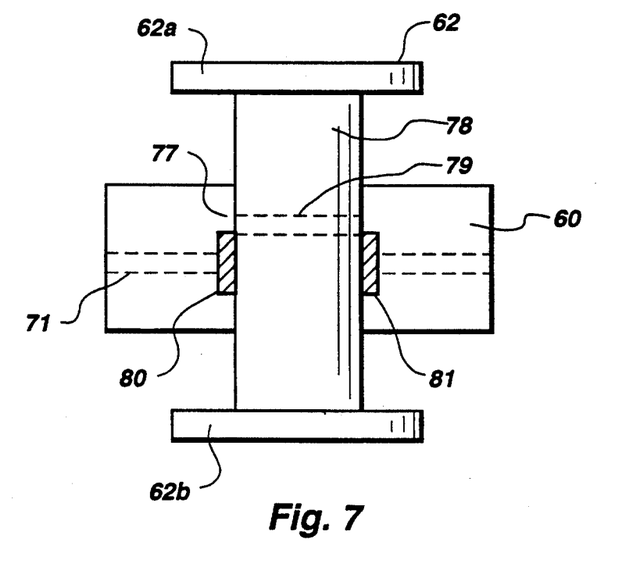
FIG. 7 is an elevation view of a slide valve member of the manifold illustrated in FIG. 6.
Figure 8:
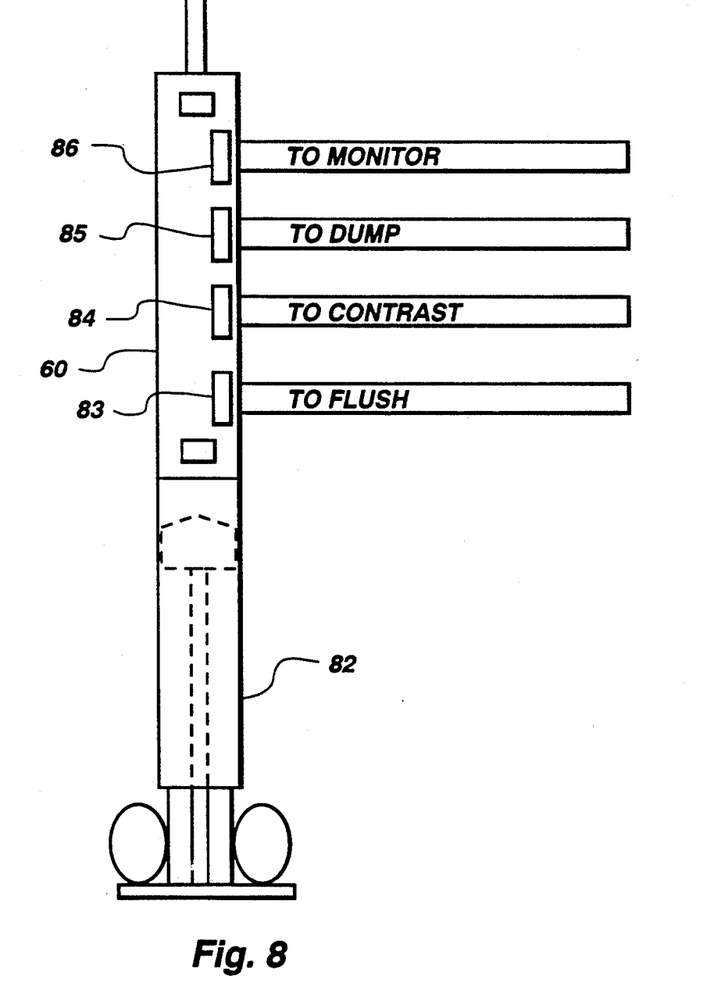
FIG. 8 is a plan view of the manifold of FIG. 6 attached to a syringe.

A preferred embodiment of a manifold having a plurality of transverse slide valve members is illustrated in FIGS. 6 through 8.

FIG. 6 is a plan view of a manifold body 60 having a plurality of top-mounted, transverse-acting valve actuators (push buttons) 61, 62, 63, 64, and 65. The manifold body 60 has a straight-through, longitudinal bore 66 preferably located on about the central longitudinal axis. An inlet valve actuator 61 controls flow of fluid from the main inlet port 67 to the central bore 66. The main inlet port 67 of the manifold is attachable to a syringe (see FIG. 8) by means of a female bayonet mount 68 which mounts securely to the male bayonet mount of a syringe.

The longitudinal bore 66 terminates at an outlet port 69 which is equipped with a luer fitting 70. An outlet valve actuator 65 controls discharge of fluid from the central bore. A plurality of transverse bores 71, 72, and 73 interconnect with the central bore 66. The transverse bores communicate with external female luer fittings 74, 75, and 76 which are capable of being connected by plastic tubing with a particular external fluid repository or fluid source (see FIG. 8). A plurality of flow-control valve actuators 62, 63, and 64 are positioned perpendicularly to the transverse (lateral) bores.

The valve actuators which are pushbutton slide valves, are positioned in the manifold body in snug-fitting passageways or cavities 77 (see FIG. 7) which pass through the manifold body. The cavities are transverse, generally perpendicular, to the lateral bores.

A slide valve actuator 62 is illustrated in a partial, sectional, elevational view in FIG. 7. The slide valve actuator has a main body (trunk) 78 which in cross-section may be round, square, or rectangular. A single transverse bore 79 (shown in dotted lines) passes through the trunk 78 of the slide valve 62. This bore 79 is adapted and positioned to interact with transverse bore 71 of the manifold body when in an open position to permit flow inward or outward to an external luer fitting (see FIG. 6). A pair of "O"-ring gaskets 80 and 81, which may be "O"-ring or elongated gasket members, are fitted in the manifold body around the transverse (lateral) bore 71 to provide for a tight fit with the trunk of the slide members to prevent fluid leakage even under high-pressure conditions.

Seal means, e.g. "O"-ring or rubber disks may be located in the slide member around the bore and at a second location displaced vertically and positioned to be in alignment with a lateral bore in the manifold body so as to seal the "off" position of the slide member.

The "O"-rings fit in a small groove around the lateral bore opening. The "O"-rings project a slight amount to form a tight seal when the cross-bore of the slide member is aligned with the lateral bore. The slide valve manifolds of the instant invention are particularly advantageous inasmuch as they are quick acting, are capable of handling high pressure fluids without leakage, and can be disassembled and sterilized if desired. A further advantage of such manifolds is that the particular flow path can be readily discerned from a quick observation or feel of the position of the single slide member or the position of various of the multiple slide members.

When the slide valve is in an off position, as shown in FIG. 7, the valve bore 79 is not aligned with transverse bore 71 of the manifold body which is then sealed off by the trunk 78 of the slide member 62 interacting with the "O"-rings 80 and 81. The slide valve 62 is fitted with touch pads 62a and 62b which also serve as stops to prevent the valve 62 from being pushed through the manifold body 60.

The manifold device is illustrated in FIG. 8 attached to a syringe 82. The manifold body 60 has four push button slide valves 83, 84, 85, and 86 which, respectively, interconnect to a flush system, to a contrast device, to a dump station, and to a monitor device.

The manifold valves of this invention having a plurality of short-stroke, pushbutton slide valves are particularly useful in conducting medical procedures rapidly, with certainty. Manifolds, especially of the type illustrated in FIGS. 6, 7 and 8 have positive acting slide valve members wherein the exact position of the valve members can be readily determined by feel.

The pushbutton slide valve members of FIG. 6 are generally two-position valves wherein the valve is either "on" or "off." In the "on" position, the bore position for the slide valve member is in alignment with the particular bore of the manifold body with which it is intended to communicate. The "on" position alignment may occur when the touch pad is against one surface of the manifold body and the "off" position occurring when the opposite touch pad is in contact with the opposed surface of the manifold body.

The certainty of a valve member position may also be accomplished by use of detents which would indicate the exact register (alignment) of a valve bore with a corresponding bore in the manifold body. The manifold body illustrated in FIGS. 6, 7 and 8 has a central longitudinal bore which has ancillary lateral bores intersecting the central bore. The valve members have "on"-"off" (two-position) capability. Thus, the positioning of the valve members is solely within the bores rather than at the intersection of the central bore and ancillary bores as was done in prior art manifolds of the type illustrated in FIG. 9.

The use of manifolds of the type described herein are used in critical medical procedures, often under conditions of subdued (dim) lighting so that cathode ray tube screens or other displays may be constantly monitored. The pushbutton valve manifolds of this invention can be efficiently and securely operated by "touch." Each valve member, for example, in the manifold of FIGS. 6, 7 and 8 has a two-position operation. For example, a quick "feel" of the pushbutton 62, 63 and 64 in FIG. 6 can tell if they are all in the "up" position ("off" position). If pushbuttons 61 and 65 are in a "down" position ("on" position), then the flow is only through the main channel as bore 66. In FIG. 8, if all pushbuttons are in an "off" position except 86 and 87, then the monitor condition is the only one operable.

In contrast to petcock valves wherein all "on" and "off" positions are in the same plane, the pushbutton valves have the "on" and "off" positions in different planes.

The manifold valves, particularly those of FIGS. 4, 5, 6, 7, and 8, may be made with a unitary body or a two-part body similar to that shown in FIGS. 1 and 2. A one-piece construction of a manifold body may be formed from a single plastic block by drilling a bore along the central longitudinal axis, then drilling the lateral bores from one side surface to interconnect with the central bore. The bores and channels, however, are preferably formed during molding of the body.

Valve member openings may be drilled transverse to the central and lateral bores. Valve members with a round cross-section, using a keyway and key to prevent rotation, may be used with such drilled valve member openings. If square valve member openings are desired, the drilled openings may be shaped. Also, square openings may be obtained by casting the plastic in uncured state in a mold which provides for the valve member openings. A preferred construction for the manifolds of the instant invention involves a modular, jigsaw-type construction.

A preferred feature of the manifold is that each bore in which high pressure fluid is present contains an "O"-ring at any junction with a slide valve wherein a solid (trunk) surface of the slide valve could be juxtaposed to the bore. The presence of an "O"-ring at such junctions prevents leakage of high pressure fluids from the manifold.

Elongated gaskets are generally preferred to "O"-ring. These gaskets have a pendant shape with an opening near one of the ends of the pendant.

The rapid action of the slide valves, their positive action and direction of "on-off" positions by feel are all advantageous features of the invention, especially as illustrated in FIGS. 4 through 8.

What is claimed:

1. A manifold-type valve which has means to interact with a syringe and various liquid media sources to inject or withdraw a selected fluid into or from a patient, comprising:
   a manifold body having a main longitudinal bore;
   an inlet opening in said manifold body communicating with a first end of said main bore;
   an outlet opening in said manifold body communicating with a second end of said main bore;
   a pair of slide valve members disposed in transverse cavities adjacent opposite ends of said manifold body, said cavities positioned to interrupt said main bore and each of said slide valve members having a cross-bore alignable with said main bore when said slide member is in a preselected position;
   at least one lateral bore communicating at a first end with said main bore and at a second end with a manifold surface parallel to said main bore; and
   a slide valve member disposed in a transverse cavity in said manifold body, said cavity positioned to interrupt a lateral bore, said slide valve member having a cross-bore alignable with said lateral bore when said slide member is in a preselected position.

2. The manifold-type valve of claim 1 wherein an "O"-ring is positioned around each lateral bore opening into a transverse cavity, said "O"-ring being adapted to seal the juncture between the trunk of said slide member and the lateral bore.

3. The manifold-type valve of claim 2 wherein said "O"-ring is located in the manifold body.

4. The manifold-type valve of claim 2 wherein said "O"-ring is located in said slide valve member.

5. The manifold-type valve of claim 4 wherein seal means are located in said slide valve member around said bore and at a second location.

* * * * *